(12) United States Patent
Filliers et al.

(10) Patent No.: US 8,765,979 B2
(45) Date of Patent: Jul. 1, 2014

(54) SYNTHESIS OF (2S-CIS)-2-(BROMOMETHYL)-2-(4-CHLOROPHENYL)-1,3 DIOXOLANE-4-METHANOL METHANESULFONATE(ESTER)

(75) Inventors: Walter Ferdinand Maria Filliers, Vremde (BE); Walter Louis Antoine Verstappen, Kontich (BE); Ronny Bellinkx, Peer (BE)

(73) Assignee: Janssen Pharmaceutica, NV (BE)

( * ) Notice: Subject to any disclaimer, the term of this patent is extended or adjusted under 35 U.S.C. 154(b) by 1253 days.

(21) Appl. No.: 12/601,555

(22) PCT Filed: May 23, 2008

(86) PCT No.: PCT/EP2008/056355
§ 371 (c)(1),
(2), (4) Date: May 2, 2011

(87) PCT Pub. No.: WO2008/145605
PCT Pub. Date: Dec. 4, 2008

(65) Prior Publication Data
US 2011/0196160 A1 Aug. 11, 2011

(30) Foreign Application Priority Data
May 25, 2007 (EP) .................................... 07108944

(51) Int. Cl.
*C07D 405/14* (2006.01)
(52) U.S. Cl.
CPC .................................... *C07D 405/14* (2013.01)
USPC ....................................................... 549/453
(58) Field of Classification Search
CPC ..................................................... C07D 405/14
USPC ....................................................... 549/453
See application file for complete search history.

(56) References Cited

FOREIGN PATENT DOCUMENTS

WO   WO 96/13499 A   5/1996
WO   WO 00/37463 A   6/2000

OTHER PUBLICATIONS

PCT Search Report and Written Opinion PCT/EP2008/056355 dated Aug. 22, 2008, 10 pages.

*Primary Examiner* — Taofiq A Solola

(57) ABSTRACT

The present invention relates to an improved process for the preparation of (2S-cis)-2-(bromomethyl)-2-(4-chlorophenyl)-1,3-dioxolane-4-methanol methanesulfonate(ester), a key intermediate for the preparation of the apoB secretion/MTP inhibitor mitratapide.

5 Claims, No Drawings

SYNTHESIS OF (2S-CIS)-2-(BROMOMETHYL)-2-(4-CHLOROPHENYL)-1,3 DIOXOLANE-4-METHANOL METHANESULFONATE(ESTER)

CROSS REFERENCE TO RELATED APPLICATIONS

This application is a national stage application of Patent Application No. PCT/EP2008/056355, filed 23 May 2008, which in turn claims the benefit of EPO Patent Application No. 07108944.5 filed 25 May 2007. The complete disclosures of the aforementioned related patent applications are hereby incorporated herein by reference for all purposes.

The present invention relates to an improved process for the preparation of (2S-cis)-2-(bromomethyl)-2-(4-chlorophenyl)-1,3-dioxolane-4-methanol methanesulfonate(ester), a key intermediate for the preparation of the apoB secretion/MTP inhibitor mitratapide.

Mitratapide is the INN (International Non Proprietary Name) for the compound (−)-[2S-[2α,4α(S*)]]-4-[4-[4-[4-[[2-(4-chlorophenyl)-2-[[(4-methyl-4H-1,2,4-triazol-3-yl)thio]methyl]-1,3-dioxolan-4-yl]methoxy]-phenyl]-1-piperazinyl]phenyl]-2,4-dihydro-2-(1-methylpropyl)-3H-1,2,4-triazol-3-one having the following structure.

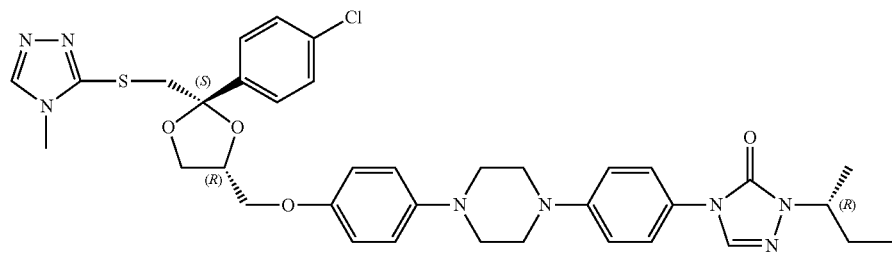

Mitratapide has been described in WO-96/13499 as compound (40) having apolipoprotein B secretion and microsomal triglyceride transfer protein inhibiting properties therefore useful as a lipid lowering agent in the treatment of obesity.

WO-00/37463 discloses S-oxide derivatives of mitratapide and a procedure to prepare (2S-cis)-2-(bromomethyl)-2-(4-chlorophenyl)-1,3-dioxolane-4-methanol methane-sulfonate (ester) as intermediate (18) in working example A.7 on page 20.

(2 S-cis)-2-(bromomethyl)-2-(4-chlorophenyl)-1,3-dioxolane-4-methanol methane-sulfonate(ester) (hereinafter referred to as "compound A") has the following structure compound A

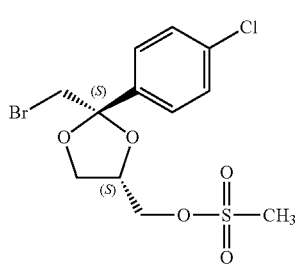

wherein the substituents on the 1,3-dioxolane ring have the (2S,4S) stereochemistry according to the Cahn-Ingold-Prelog nomenclature.

Since two of the three chiral carbon atoms of mitratapide are located on the 1,3-dioxolane ring an efficient synthesis of compound A is therefore highly desirable.

The preparation of compound A has been described in WO-00/37463 in Examples A.6 and A.7 as follows:

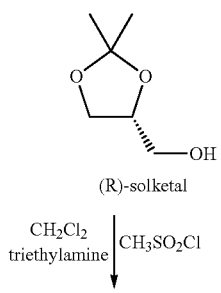

(R)-solketal $\begin{array}{c} CH_2Cl_2 \\ triethylamine \end{array} \Big| CH_3SO_2Cl$

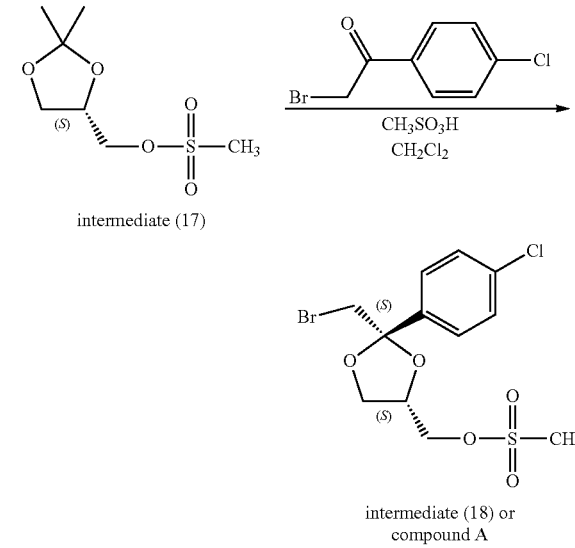

Compound A was obtained with a yield of 23.7% according to the procedure of Example A.7 in WO-00/37463, i.e. reaction of (2S)-2,2-dimethyl-1,3-dioxolane-4-methanol methanesulfonate(ester) with 2-bromo-1-(4-chloro-phenyl)-ethanone in dichloromethane as solvent.

Unexpectedly, it has now been found that the yield of said reaction can be markedly improved by performing the same reaction in the absence of a solvent while bubbling nitrogen through the reaction mixture or applying underpressure to remove the acetone formed during the said reaction.

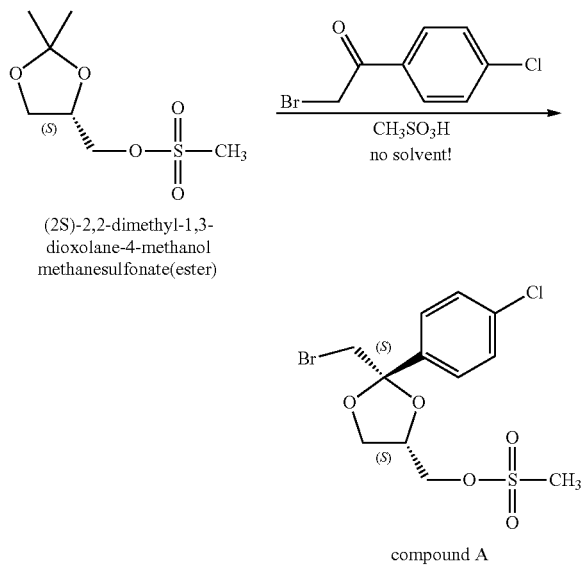

(2S)-2,2-dimethyl-1,3-dioxolane-4-methanol methanesulfonate(ester)

compound A

As demonstrated further in Example 1 of the Experimental Part, the improved procedure for preparing "compound A" has a yield of 64.8% which is an almost threefold increase over the prior art method yield of 23.7%.

Methanesulfonic acid is used in the reaction as a catalyst. Other suitable catalysts are p-toluenesulfonic acid monohydrate, hydrogen chloride, sulfuric acid, phosphoric acid, nitric acid, formic acid, trifluoroacetic acid, camphorsulfonic acid, hydrogen chloride in 2-propanol solution, and hydrogen bromide in acetic acid solution or propionic acid solution.

The reaction product obtained from this reaction can be purified by crystallisation from a suitable organic solvent such as ethanol, 2-propanol, methyl tert-butyl ether, or ethyl acetate.

Further purification can be done by dissolving the product obtained after crystallisation in diisopropylether until a homogeneous solution is obtained, stirring said solution for 7 days and adding methanol to said solution and filtering off the precipitate.

EXPERIMENTAL PART

Example 1

A mixture of (2S)-2,2-dimethyl-1,3-dioxolane-4-methanol methanesulfonate(ester) (1 mol), 2-bromo-1-(4-chlorophenyl)-ethanone (0.8 mol) was stirred in a flask. Methanesulfonic acid (0.24 mol) was added and the reaction mixture was stirred while nitrogen was bubbled through the reaction mixture (alternatively the reaction mixture may also be stirred under vacuum). After six hours, stirring of the reaction mixture was stopped and the reaction mixture was left overnight. Ethyl acetate (1500 ml) was added and the mixture was stirred until it became homogeneous. The reaction mixture was then washed successively with water (200 ml), an aqueous $Na_2CO_3$ solution (150 ml), and water (150 ml). The organic layer was evaporated till dryness and the residue was crystallised from ethanol (1 liter), yielding a solid residue. This residue was dissolved in diisopropylether (DIPE) and stirred for one week. Then methanol was added and after stirring for two hours, the precipitate was filtered off and dried, yielding 250.1 g (64.8%) of (2S-cis)-2-(bromomethyl)-2-(4-chlorophenyl)-1,3-dioxolane-4-methanol methane-sulfonate(ester).

Chromatographic analysis by GC (HP5-column, length: 25 m, ID 320 μm; film thickness 0.52 μm; on column; initial temperature: 50° C.; heating at 10° C./min to 300° C.) showed said (2S-cis)-2-(bromomethyl)-2-(4-chlorophenyl)-1,3-dioxolane-4-methanol methane-sulfonate(ester) had a purity of more than 95% of the cis-stereoisomer and less than 5% of the trans-stereoisomer.

The invention claimed is:

1. A process for preparing (2S-cis)-2-(bromomethyl)-2-(4-chlorophenyl)-1,3-dioxolane-4-methanol methane-sulfonate (ester) by reacting (2S)-2,2-dimethyl-1,3-dioxolane-4-methanol methanesulfonate(ester) with 2-bromo-1-(4-chloro-phenyl)-ethanone in the presence of a catalyst characterized in that the reaction is performed in the absence of a solvent while nitrogen is bubbled through the reaction mixture or an underpressure is applied.

2. A process according to claim 1 wherein the catalyst is selected from methanesulfonic acid, p-toluenesulfonic acid monohydrate, hydrogen chloride, sulfuric acid, phosphoric acid, nitric acid, formic acid, trifluoroacetic acid, camphorsulfonic acid, hydrogen chloride in 2-propanol solution, and hydrogen bromide in acetic acid solution or propionic acid solution.

3. A process according to claim 2 wherein the catalyst is methanesulfonic acid.

4. A process whereby the product obtained by the process according to claim 1 is purified by crystallisation from an organic solvent selected from ethanol, 2-propanol, methyl tert-butyl ether, or ethyl acetate.

5. A process whereby the product obtained by the process of claim 4 is purified by dissolving it in diisopropylether until a homogeneous solution is obtained, stirring said solution for 7 days and adding methanol to said solution and filtering off the precipitate.

* * * * *